(12) United States Patent
Govari et al.

(10) Patent No.: US 8,784,413 B2
(45) Date of Patent: *Jul. 22, 2014

(54) CATHETER WITH PRESSURE SENSING

(71) Applicant: Biosense Webster (Israel), Ltd., Yokneam (IL)

(72) Inventors: Assaf Govari, Haifa (IL); Andres Claudio Altmann, Haifa (IL); Yaron Ephrath, Karkur (IL); Yitzhack Schwartz, Haifa, IL (US)

(73) Assignee: Biosense Webster (Israel) Ltd. (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/705,518

(22) Filed: Dec. 5, 2012

(65) Prior Publication Data

US 2013/0096551 A1  Apr. 18, 2013

Related U.S. Application Data

(63) Continuation of application No. 11/868,733, filed on Oct. 8, 2007, now Pat. No. 8,357,152.

(51) Int. Cl.
*A61B 18/18* (2006.01)
*A61B 5/05* (2006.01)

(52) U.S. Cl.
USPC ............... 606/41; 600/12; 600/145; 600/424

(58) Field of Classification Search
CPC .... A61B 1/00158; A61B 5/062; A61B 5/065; A61B 8/42; A61B 8/4245; A61B 8/4254; A61B 8/4263; A61B 18/04; A61B 18/08; A61B 18/082; A61B 18/12; A61B 18/14; A61B 18/1477–18/1482; A61B 18/18; A61B 2562/0223

USPC .................. 606/34, 41, 47; 600/12, 145, 424
See application file for complete search history.

(56) References Cited

U.S. PATENT DOCUMENTS 3,841,150 A   10/1974  Pearson
3,971,364 A   7/1976   Fletcher et al.
(Continued)

FOREIGN PATENT DOCUMENTS

DE   19750441 A   6/1999
EP   928601 A1    7/1999
(Continued)

OTHER PUBLICATIONS

Biter, William J. et al., "Magnetic Wire Strain Sensor", 33rd International Sampe Technical Conference, Nov. 5-8, 2001, vol. 33, pp. 12-23, Seattle, WA.

(Continued)

*Primary Examiner* — Michael Peffley
*Assistant Examiner* — Khadijeh Vahdat

(57) ABSTRACT

A medical probe includes a flexible insertion tube, having a distal end for insertion into a body cavity of a patient, and a distal tip, which is disposed at the distal end of the insertion tube and is configured to be brought into contact with tissue in the body cavity. A resilient member couples the distal tip to the distal end of the insertion tube and is configured to deform in response to pressure exerted on the distal tip when the distal tip engages the tissue. A position sensor within the probe senses a position of the distal tip relative to the distal end of the insertion tube, which changes in response to deformation of the resilient member.

16 Claims, 2 Drawing Sheets

(56) References Cited

U.S. PATENT DOCUMENTS

| | | | |
|---|---|---|---|
| 4,764,114 | A | 8/1988 | Jeffcoat et al. |
| 4,856,993 | A | 8/1989 | Maness et al. |
| 4,930,494 | A | 6/1990 | Takehana et al. |
| 5,263,493 | A | 11/1993 | Avitall |
| 5,368,564 | A | 11/1994 | Savage |
| 5,391,199 | A | 2/1995 | Ben-Haim |
| 5,462,527 | A | 10/1995 | Stevens-Wright et al. |
| 5,487,757 | A | 1/1996 | Truckai et al. |
| 5,499,542 | A | 3/1996 | Morlan |
| 5,542,434 | A | 8/1996 | Imran et al. |
| 5,558,091 | A | 9/1996 | Acker et al. |
| 5,563,354 | A | 10/1996 | Kropp |
| 5,662,124 | A | 9/1997 | Wilk |
| 5,673,695 | A | 10/1997 | McGee et al. |
| 5,680,860 | A | 10/1997 | Imran |
| 5,685,878 | A | 11/1997 | Falwell et al. |
| 5,728,149 | A | 3/1998 | Laske et al. |
| 5,769,843 | A | 6/1998 | Abela et al. |
| 5,826,576 | A | 10/1998 | West |
| 5,833,608 | A | 11/1998 | Acker |
| 5,836,894 | A | 11/1998 | Sarvazyan |
| 5,860,974 | A | 1/1999 | Abele |
| 5,861,024 | A | 1/1999 | Rashidi |
| 5,902,248 | A | 5/1999 | Millar et al. |
| 5,916,147 | A | 6/1999 | Boury |
| 5,944,022 | A | 8/1999 | Nardella et al. |
| 5,947,320 | A | 9/1999 | Bordner et al. |
| 5,964,757 | A | 10/1999 | Ponzi |
| 5,974,320 | A | 10/1999 | Ward et al. |
| 5,983,126 | A | 11/1999 | Wittkampf |
| 6,048,329 | A | 4/2000 | Thompson et al. |
| 6,063,022 | A * | 5/2000 | Ben-Haim ................ 600/41 |
| 6,123,699 | A | 9/2000 | Webster, Jr. |
| 6,171,277 | B1 | 1/2001 | Ponzi |
| 6,177,792 | B1 * | 1/2001 | Govari et al. ............ 324/207.12 |
| 6,183,463 | B1 | 2/2001 | Webster, Jr. |
| 6,198,974 | B1 | 3/2001 | Webster, Jr. |
| 6,201,387 | B1 | 3/2001 | Govari |
| 6,203,493 | B1 | 3/2001 | Ben-Haim |
| 6,216,027 | B1 | 4/2001 | Willis et al. |
| 6,226,542 | B1 | 5/2001 | Reisfeld |
| 6,239,724 | B1 | 5/2001 | Doron et al. |
| 6,241,724 | B1 | 6/2001 | Fleischman et al. |
| 6,266,551 | B1 | 7/2001 | Osadchy et al. |
| 6,272,371 | B1 * | 8/2001 | Shlomo ................ 600/424 |
| 6,272,672 | B1 | 8/2001 | Conway |
| 6,301,496 | B1 | 10/2001 | Reisfeld |
| 6,332,089 | B1 | 12/2001 | Acker et al. |
| 6,334,837 | B1 | 1/2002 | Hein et al. |
| 6,335,617 | B1 | 1/2002 | Osadchy et al. |
| 6,351,549 | B1 | 2/2002 | Souluer |
| 6,436,059 | B1 | 8/2002 | Zanelli |
| 6,456,864 | B1 | 9/2002 | Swanson et al. |
| 6,484,118 | B1 * | 11/2002 | Govari ................ 702/150 |
| 6,551,302 | B1 | 4/2003 | Rosinko et al. |
| 6,569,098 | B2 | 5/2003 | Kawchuk |
| 6,574,492 | B1 | 6/2003 | Ben-Haim et al. |
| 6,584,856 | B1 | 7/2003 | Biter et al. |
| 6,602,242 | B1 | 8/2003 | Fung et al. |
| 6,612,992 | B1 | 9/2003 | Hossack et al. |
| 6,618,612 | B1 | 9/2003 | Acker et al. |
| 6,690,963 | B2 | 2/2004 | Ben-Haim et al. |
| 6,695,808 | B2 | 2/2004 | Tom |
| 6,711,429 | B1 | 3/2004 | Gilboa et al. |
| 6,727,371 | B2 | 4/2004 | Müller et al. |
| 6,814,733 | B2 | 11/2004 | Schwartz et al. |
| 6,835,173 | B2 | 12/2004 | Couvillon, Jr. |
| 6,892,091 | B1 * | 5/2005 | Ben-Haim et al. ............ 600/509 |
| 6,915,149 | B2 | 7/2005 | Ben-Haim |
| 6,945,956 | B2 | 9/2005 | Waldhauser et al. |
| 6,964,205 | B2 | 11/2005 | Papakostas et al. |
| 6,973,339 | B2 | 12/2005 | Govari |
| 6,997,924 | B2 | 2/2006 | Schwartz et al. |
| 7,077,823 | B2 | 7/2006 | McDaniel |
| 7,156,816 | B2 | 1/2007 | Schwartz et al. |
| 7,235,070 | B2 | 6/2007 | Vanney |
| 7,297,116 | B2 | 11/2007 | Varghese et al. |
| 7,306,593 | B2 | 12/2007 | Keidar et al. |
| 7,306,599 | B2 | 12/2007 | Karasawa et al. |
| 7,311,704 | B2 | 12/2007 | Paul et al. |
| 7,397,364 | B2 | 7/2008 | Govari |
| 7,435,232 | B2 | 10/2008 | Liebschner |
| 7,465,288 | B2 | 12/2008 | Dudney et al. |
| 7,481,774 | B2 | 1/2009 | Brockway et al. |
| 7,536,218 | B2 | 5/2009 | Govari et al. |
| 7,604,605 | B2 | 10/2009 | Zvuloni |
| 7,662,151 | B2 | 2/2010 | Crompton, Jr. et al. |
| 7,681,432 | B2 | 3/2010 | Hay et al. |
| 7,686,767 | B2 | 3/2010 | Maschke |
| 7,914,440 | B2 | 3/2011 | Otawara |
| 7,959,601 | B2 | 6/2011 | McDaniel et al. |
| 7,984,659 | B2 | 7/2011 | Fujimoto et al. |
| 8,043,216 | B2 | 10/2011 | Matsumura |
| 8,046,049 | B2 | 10/2011 | Govari et al. |
| 8,083,691 | B2 | 12/2011 | Goldenberg et al. |
| 8,137,275 | B2 | 3/2012 | Fan et al. |
| 8,374,819 | B2 | 2/2013 | Govari et al. |
| 2001/0047129 | A1 | 11/2001 | Hall et al. |
| 2001/0047133 | A1 | 11/2001 | Gilboa et al. |
| 2002/0002329 | A1 | 1/2002 | Avitall |
| 2002/0065455 | A1 * | 5/2002 | Ben-Haim et al. ............ 600/407 |
| 2002/0068866 | A1 | 6/2002 | Zikorus et al. |
| 2002/0068931 | A1 | 6/2002 | Wong et al. |
| 2002/0165461 | A1 | 11/2002 | Hayzelden et al. |
| 2002/0193781 | A1 | 12/2002 | Loeb |
| 2003/0120150 | A1 * | 6/2003 | Govari ................ 600/424 |
| 2003/0120195 | A1 | 6/2003 | Milo et al. |
| 2003/0130615 | A1 | 7/2003 | Tom |
| 2003/0158494 | A1 | 8/2003 | Dahl et al. |
| 2003/0187389 | A1 | 10/2003 | Morency et al. |
| 2004/0049255 | A1 | 3/2004 | Jain et al. |
| 2004/0064024 | A1 | 4/2004 | Sommer |
| 2004/0068178 | A1 | 4/2004 | Govari |
| 2004/0097806 | A1 | 5/2004 | Hunter et al. |
| 2004/0102769 | A1 | 5/2004 | Schwartz et al. |
| 2004/0147920 | A1 * | 7/2004 | Keidar ................ 606/34 |
| 2004/0244464 | A1 | 12/2004 | Hajdukiewicz et al. |
| 2004/0254458 | A1 | 12/2004 | Govari |
| 2005/0033135 | A1 | 2/2005 | Govari |
| 2005/0080429 | A1 | 4/2005 | Freyman et al. |
| 2005/0096590 | A1 | 5/2005 | Gullickson et al. |
| 2005/0228274 | A1 | 10/2005 | Boese et al. |
| 2005/0277875 | A1 | 12/2005 | Selkee |
| 2006/0009690 | A1 | 1/2006 | Fuimaono et al. |
| 2006/0009735 | A1 | 1/2006 | Viswanathan et al. |
| 2006/0015096 | A1 * | 1/2006 | Hauck et al. ................ 606/41 |
| 2006/0064038 | A1 | 3/2006 | Omata et al. |
| 2006/0074297 | A1 | 4/2006 | Viswanathan |
| 2006/0173480 | A1 | 8/2006 | Zhang |
| 2006/0184106 | A1 | 8/2006 | McDaniel et al. |
| 2006/0200049 | A1 | 9/2006 | Leo et al. |
| 2006/0247618 | A1 * | 11/2006 | Kaplan et al. ................ 606/41 |
| 2007/0060832 | A1 | 3/2007 | Levin |
| 2007/0060847 | A1 | 3/2007 | Leo et al. |
| 2007/0100332 | A1 | 5/2007 | Paul et al. |
| 2007/0106114 | A1 * | 5/2007 | Sugimoto et al. ............ 600/117 |
| 2007/0106115 | A1 | 5/2007 | Sugimoto et al. |
| 2007/0142749 | A1 | 6/2007 | Khatib et al. |
| 2007/0151391 | A1 | 7/2007 | Larkin et al. |
| 2007/0156114 | A1 | 7/2007 | Worley et al. |
| 2007/0161882 | A1 | 7/2007 | Pappone |
| 2007/0167740 | A1 | 7/2007 | Grunewald et al. |
| 2007/0167818 | A1 | 7/2007 | Osborn et al. |
| 2007/0179492 | A1 | 8/2007 | Pappone |
| 2007/0185397 | A1 | 8/2007 | Govari et al. |
| 2007/0191829 | A1 * | 8/2007 | McGee et al. ................ 606/41 |
| 2007/0197927 | A1 | 8/2007 | Ofek et al. |
| 2007/0197939 | A1 | 8/2007 | Wallace et al. |
| 2007/0282211 | A1 | 12/2007 | Ofek et al. |
| 2008/0009750 | A1 | 1/2008 | Aeby et al. |
| 2008/0015568 | A1 | 1/2008 | Paul et al. |
| 2008/0051704 | A1 * | 2/2008 | Patel et al. ................ 604/95.05 |
| 2008/0065111 | A1 | 3/2008 | Blumenkranz et al. |
| 2008/0071267 | A1 | 3/2008 | Wang et al. |

(56) References Cited

U.S. PATENT DOCUMENTS

| | | | |
|---|---|---|---|
| 2008/0077049 A1 | 3/2008 | Hirshman | |
| 2008/0146918 A1 | 6/2008 | Magnin et al. | |
| 2008/0183075 A1* | 7/2008 | Govari et al. | 600/437 |
| 2008/0200843 A1 | 8/2008 | Williams et al. | |
| 2008/0249467 A1 | 10/2008 | Burnett et al. | |
| 2008/0249522 A1 | 10/2008 | Pappone et al. | |
| 2008/0255540 A1 | 10/2008 | Selkee | |
| 2008/0269606 A1 | 10/2008 | Matsumura | |
| 2008/0275428 A1* | 11/2008 | Tegg et al. | 604/533 |
| 2008/0275442 A1 | 11/2008 | Paul et al. | |
| 2008/0275465 A1 | 11/2008 | Paul et al. | |
| 2008/0281319 A1 | 11/2008 | Paul et al. | |
| 2008/0287777 A1 | 11/2008 | Li et al. | |
| 2008/0288038 A1 | 11/2008 | Paul et al. | |
| 2008/0294144 A1 | 11/2008 | Leo et al. | |
| 2008/0294158 A1 | 11/2008 | Pappone et al. | |
| 2009/0010021 A1 | 1/2009 | Smith et al. | |
| 2009/0093806 A1 | 4/2009 | Govari et al. | |
| 2009/0138007 A1 | 5/2009 | Govari et al. | |
| 2009/0158511 A1 | 6/2009 | Maze et al. | |
| 2009/0177111 A1 | 7/2009 | Miller et al. | |
| 2009/0275966 A1 | 11/2009 | Mitusina | |
| 2009/0287118 A1 | 11/2009 | Malek | |
| 2009/0294361 A1 | 12/2009 | Larsen | |
| 2009/0306515 A1 | 12/2009 | Matsumura et al. | |
| 2009/0306650 A1 | 12/2009 | Govari et al. | |
| 2010/0063478 A1 | 3/2010 | Selkee | |
| 2010/0069921 A1 | 3/2010 | Miller et al. | |
| 2010/0121138 A1 | 5/2010 | Goldenberg et al. | |
| 2010/0137845 A1 | 6/2010 | Ramstein et al. | |
| 2010/0152574 A1 | 6/2010 | Erdman et al. | |
| 2010/0160770 A1 | 6/2010 | Govari et al. | |
| 2010/0160778 A1 | 6/2010 | Eskandari et al. | |
| 2010/0168620 A1 | 7/2010 | Klimovitch et al. | |
| 2010/0168918 A1 | 7/2010 | Zhao et al. | |
| 2010/0292566 A1 | 11/2010 | Nagano et al. | |
| 2010/0298826 A1 | 11/2010 | Leo et al. | |
| 2011/0054354 A1 | 3/2011 | Hunter et al. | |
| 2011/0054355 A1 | 3/2011 | Hunter et al. | |
| 2011/0071436 A1 | 3/2011 | Althoefer et al. | |
| 2011/0130648 A1 | 6/2011 | Beeckler et al. | |
| 2011/0153252 A1 | 6/2011 | Govari et al. | |
| 2011/0153253 A1 | 6/2011 | Govari et al. | |
| 2011/0160556 A1 | 6/2011 | Govari | |
| 2011/0172538 A1 | 7/2011 | Sumi | |
| 2011/0184406 A1 | 7/2011 | Selkee | |
| 2011/0307207 A1 | 12/2011 | Govari et al. | |
| 2012/0004576 A1 | 1/2012 | Govari et al. | |
| 2012/0041295 A1 | 2/2012 | Schultz | |
| 2012/0089358 A1 | 4/2012 | Ludwin et al. | |
| 2012/0108988 A1 | 5/2012 | Ludwin et al. | |
| 2012/0149966 A1 | 6/2012 | Ludwin et al. | |
| 2012/0149967 A1 | 6/2012 | Ludwin et al. | |
| 2012/0150075 A1 | 6/2012 | Ludwin et al. | |
| 2012/0184864 A1 | 7/2012 | Harlev et al. | |
| 2012/0184865 A1 | 7/2012 | Harlev et al. | |
| 2012/0253167 A1 | 10/2012 | Bonyak et al. | |
| 2012/0259194 A1 | 10/2012 | Selkee | |
| 2012/0271145 A1 | 10/2012 | Govari et al. | |
| 2012/0310116 A1 | 12/2012 | Ludwin et al. | |
| 2012/0316407 A1 | 12/2012 | Anthony et al. | |
| 2013/0018306 A1 | 1/2013 | Ludwin | |

FOREIGN PATENT DOCUMENTS

| | | |
|---|---|---|
| EP | 980693 A1 | 2/2000 |
| EP | 1502555 A1 | 2/2005 |
| EP | 1586281 A1 | 10/2005 |
| EP | 1690564 A1 | 8/2006 |
| EP | 1743575 A2 | 1/2007 |
| EP | 1820464 A1 | 8/2007 |
| EP | 1897581 A2 | 3/2008 |
| EP | 2000789 A2 | 12/2008 |
| EP | 2047797 A2 | 4/2009 |
| EP | 2127604 A1 | 12/2009 |
| EP | 2130508 B1 | 12/2009 |
| EP | 2196143 A1 | 6/2010 |
| EP | 2305115 A1 | 4/2011 |
| EP | 2338412 A1 | 6/2011 |
| EP | 2172240 B1 | 12/2012 |
| EP | 2338411 B1 | 11/2013 |
| JP | 8243168 A | 9/1996 |
| JP | 2000126301 A | 5/2000 |
| JP | 2000508224 A | 7/2000 |
| JP | 2005040215 | 2/2005 |
| JP | 2005237964 A | 9/2005 |
| JP | 2005345215 A | 12/2005 |
| JP | 2006064465 A | 3/2006 |
| JP | 2006255401 A | 9/2006 |
| JP | 2007181696 A | 7/2007 |
| WO | WO 94/17856 A1 | 8/1994 |
| WO | WO 95/10326 A | 4/1995 |
| WO | WO 96/05768 A | 2/1996 |
| WO | WO 97/29678 A | 8/1997 |
| WO | WO 97/29709 A | 8/1997 |
| WO | WO 97/29710 A | 8/1997 |
| WO | WO 98/29032 A | 7/1998 |
| WO | WO 03/020139 A | 3/2003 |
| WO | WO 2006/029563 A | 3/2006 |
| WO | WO 2006/086152 A | 8/2006 |
| WO | WO 2006/092563 A | 9/2006 |
| WO | WO 2006/135483 A2 | 12/2006 |
| WO | WO 2007/015139 A2 | 2/2007 |
| WO | WO 2007/025230 A | 3/2007 |
| WO | WO 2007/050960 A | 5/2007 |
| WO | WO 2007/067938 A | 6/2007 |
| WO | WO 2007/076312 A2 | 7/2007 |
| WO | WO 2007/082216 A | 7/2007 |
| WO | WO 2007/098494 A1 | 8/2007 |
| WO | WO 2007/111182 A | 10/2007 |
| WO | WO 2008/053402 A1 | 5/2008 |
| WO | WO 2008/147599 A1 | 12/2008 |
| WO | WO 2009/065140 A1 | 5/2009 |
| WO | WO 2009/078280 A | 6/2009 |
| WO | WO 2009/085470 A | 7/2009 |
| WO | WO 2009/147399 A | 12/2009 |
| WO | WO 2010/008975 A | 1/2010 |
| WO | WO 2011/046874 A1 | 4/2011 |

OTHER PUBLICATIONS

Biter, William J. et al., "Magnetic Wire for Monitoring Strain in Composites", Sensors, Jun. 2001, www.sensormag.com, pp. 110-114.

Guo, Shuxiang et al., "Control and Experimental results of a Catheter Operating System", Feb. 21-26, 2009, Proceedings of the 2008 IEEE, International Conference on Robotics and Biomimetics, Bankok, Thailand, pp. 91-95.

Instron Marketing Brochure, "Medical Device Testing Systems", Instron 2007 http://web.archive.org/web/20080318092822/http://www.instron.com.tr/wa/library/streamfile.aspx?doc=1678&downland=true.

Instron, "Series 3300 Load Frames, Reference Manual Equipment", Instron, pp. 1-5 and 1-10, 2004.

Kanagaratnam, Prapa et. al., "Experience of robotic catheter ablation in humans using novel remotely steerable catheter sheath", Journal of Interventional Cardiac Electrophysiology. vol. 21, No. 1, p. 19-26 (2008).

Okumura, M.D. Yasuo et al. "A Systematic Analysis of in Vivo Contact Forces on Virtual Catheter Tip/Tissue Surface Contact during Cardiac Mapping and Intervention", Journal of Cardiovascular Electrophysiology, Jun. 2008, pp. 632-640, vol. 19, No. 6.

Peirs, J. et al., "Design of an Optical Force Sensor for Force Feedback during Minimally Invasive Robotic Surgery", Eurosensors XVII, 2003, pp. 1063-1066, http:/ /mech.kuleuven.be/micro/pub/medic/Paper Eurosensors 2003 MIS sensor.extended.pdf.

Partial European Search Report mailed on Sep. 18, 2009 from corresponding European Patent Application No. 08253265.6.

Partial European Search Report mailed on Dec. 7, 2009 from related European Patent Application No. 09251502.2.

(56) References Cited

OTHER PUBLICATIONS

European Search Report mailed on Mar. 8, 2010 from related European Patent Application No. 09252143.4.
Partial European Search Report mailed on Mar. 29, 2010 from related European Patent Application No. 09252879.3.
Partial European Search Report mailed on Apr. 1, 2010 from corresponding European Patent Application No. 09252721.7.
European Search Report mailed on Mar. 2, 2011 from related European Patent Application No. 10175931.4.
European Search Report mailed on Mar. 28, 2011 from related European Patent Application No. 10252189.5.
European Search Report mailed on Mar. 28, 2011 from related European Patent Application No. 10252191.1.
European Search Report mailed on Mar. 30, 2011 from related European Patent Application No. 10252020.2.
European Search Report mailed on May 16, 2011 from related European Patent Application No. 10252232.3.
European Search Report mailed on Aug. 5, 2011 from corresponding European Patent Application No. 11158804.2.
European Search Report mailed on Sep. 20, 2011 from related European Patent Application No. 11250066.5.
European Search Report mailed on Sep. 23, 2011 from related European Patent Application No. 11169251.3.
European Search Report mailed on Oct. 28, 2011 from related European Patent Application No. 11171842.5.
European Search Report mailed on Nov. 17, 2011 from related European Patent Application No. 11177600.1.
European Search Report mailed on Feb. 15, 2012 from related European Patent Application No. 11182854.7.
European Search Report mailed on May 2, 2012 from related European Patent Application No. 11189326.9.
European Search Report mailed on Jun. 4, 2012 from corresponding European Patent Application No. 12163784.7.
European Search Report mailed on Jul. 20, 2012 from related European Patent Application No. 12161784.9.
European Search Report mailed on Nov. 20, 2012 from related European Patent Application No. 12176163.9.
European Search Report mailed on Feb. 11, 2013 from related European Patent Application No. 11187525.8.
European Search Report mailed on Apr. 9, 2013 from related European Patent Application No. 13150145.4.

* cited by examiner

US 8,784,413 B2

CATHETER WITH PRESSURE SENSING

CROSS REFERENCE TO RELATED APPLICATION

This application is a continuation of application Ser. No. 11/868,733 filed on Oct. 8, 2007, now U.S. Pat. No. 8,357,152 which is assigned to the assignee of the present patent application and whose disclosure is incorporated herein by reference.

FIELD OF THE INVENTION

The present invention relates generally to invasive medical devices, and specifically to methods and devices for sensing pressure exerted against a probe, such as a catheter, inside the body of a patient.

BACKGROUND OF THE INVENTION

Intracardiac radio-frequency (RF) ablation is a well-known method for treating cardiac arrhythmias. Typically, a catheter having an electrode at its distal tip is inserted through the patient's vascular system into a chamber of the heart. The electrode is brought into contact with a site (or sites) on the endocardium, and RF energy is applied through the catheter to the electrode in order to ablate the heart tissue at the site. It is important to ensure proper contact between the electrode and the endocardium during ablation in order to achieve the desired therapeutic effect without excessive damage to the tissue.

Various techniques have been suggested for verifying electrode contact with the tissue. For example, U.S. Pat. No. 6,695,808, whose disclosure is incorporated herein by reference, describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. Pat. No. 6,241,724, whose disclosure is incorporated herein by reference, describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey RF energy to these elements, and not to other elements that are in contact only with blood.

A further example is presented in U.S. Pat. No. 6,915,149, whose disclosure is incorporated herein by reference. This patent describes a method for mapping a heart using a catheter having a tip electrode for measuring the local electrical activity. In order to avoid artifacts that may arise from poor tip contact with the tissue, the contact pressure between the tip and the tissue is measured using a pressure sensor to ensure stable contact.

U.S. Patent Application Publication 2007/0100332, whose disclosure is incorporated herein by reference, describes systems and methods for assessing electrode-tissue contact for tissue ablation. An electro-mechanical sensor within the catheter shaft generates electrical signals corresponding to the amount of movement of the electrode within a distal portion of the catheter shaft. An output device receives the electrical signals for assessing a level of contact between the electrode and a tissue.

SUMMARY OF THE INVENTION

The embodiments of the present invention that are described hereinbelow provide a novel design of an invasive probe, such as a catheter, as well as systems and methods making use of such a probe. The design is particularly useful in achieving and verifying proper contact between the distal tip of the probe and tissue that the probe engages inside the body.

In some embodiments, the probe comprises a flexible insertion tube, having a distal end for insertion into a body cavity of a patient. The distal tip of the probe is coupled to the distal end of the insertion tube by a resilient member, such as a spring, which deforms in response to pressure exerted on the distal tip when it engages the tissue. A position sensor within the probe senses the position of the distal tip relative to the distal end of the insertion tube, which is indicative of deformation of the resilient member, and is thus able to give an indication of the pressure.

In a disclosed embodiment, the sensor may comprise a magnetic field sensor in the distal tip, and the probe may thus be used as part of a system that determines the coordinates of the distal tip within the body using magnetic fields. For this purpose, a first magnetic field generator, disposed outside the body of the patient, generates a magnetic field within the body. The distal end of the insertion tube contains a second (typically much smaller) magnetic field generator. The sensor in the distal tip generates signals responsively to the magnetic fields of both the first and second field generators. These signals are processed both to determine coordinates of the distal tip within the body and to detect changes in the position of the distal tip relative to the distal end of the insertion tube, which are indicative of deformation of the resilient member and hence of the pressure exerted on the distal tip.

Alternatively, the distal tip may contain a magnetic field generator, and the field that it generates may be measured by sensors in the distal end of the insertion tube and outside the body for the purposes of detection of sensing pressure on and position coordinates of the distal tip.

There is therefore provided, in accordance with an embodiment of the present invention, a medical probe, including:

a flexible insertion tube, having a distal end for insertion into a body cavity of a patient;

a distal tip, which is disposed at the distal end of the insertion tube and is configured to be brought into contact with tissue in the body cavity;

a resilient member, which couples the distal tip to the distal end of the insertion tube and is configured to deform in response to pressure exerted on the distal tip when the distal tip engages the tissue; and a position sensor within the probe for sensing a position of the distal tip relative to the distal end of the insertion tube, which changes in response to deformation of the resilient member.

In disclosed embodiments, the position sensor is configured to generate a signal indicative of an axial displacement and an orientation of the distal tip relative to the distal end of the insertion tube. In some embodiments, the position sensor is configured to generate the signal responsively to a magnetic field that is generated in a vicinity of the distal tip. In one embodiment, the position sensor is disposed in the distal end of the insertion tube, and the probe includes a magnetic field generator within the distal tip for generating the magnetic field. In another embodiment, the position sensor is disposed in the distal tip, and the probe includes a magnetic field generator within the distal end of the insertion tube for generating the magnetic field. Typically, the position sensor and the magnetic field generator include coils.

In one embodiment, the resilient member includes a spring, and the position sensor is configured to generate a signal, responsively to the deformation, which is indicative of the pressure exerted on the distal tip.

In a disclosed embodiment, the distal tip includes an electrode, which is configured to make electrical contact with the tissue, wherein the electrode is coupled to apply electrical energy to the tissue so as to ablate a region of the tissue.

There is also provided, in accordance with an embodiment of the present invention, apparatus for performing a medical procedure inside a body of a patient, the apparatus including:

a first magnetic field generator, for disposition outside the body of the patient, for generating a first magnetic field within the body;

a probe, which includes:
an insertion tube having a distal end for insertion into a body cavity of a patient;
a second magnetic field generator within the distal end of the insertion tube for generating a second magnetic field;
a distal tip, which is flexibly coupled to the distal end of the insertion tube; and
a sensor, which is disposed within the distal tip and is configured to generate first and second signals responsively to the first and second magnetic fields, respectively; and a processor, which is coupled to receive and process the first signal so as to determine coordinates of the distal tip within the body and to receive and process the second signal so as to detect changes in a position of the distal tip relative to the distal end of the insertion tube.

In some embodiments, the distal tip is rigid, and the probe includes a resilient member, which couples the distal tip to the distal end of the insertion tube. Typically, the resilient member is configured to deform in response to pressure exerted on the distal tip when the distal tip engages tissue inside the body, and the changes in the position of the distal tip are indicative of deformation of the resilient member, while the processor is configured to generate, responsively to the deformation, an output that is indicative of the pressure exerted on the distal tip. Optionally, the processor may be configured to generate a control input for automatically controlling motion of the probe within the body cavity responsively to the first and second signals.

There is additionally provided, in accordance with an embodiment of the present invention, a method for contacting tissue in a body cavity of a patient, the method including:

inserting a probe into the body cavity, the probe including a flexible insertion tube and a distal tip, which is coupled to a distal end of the insertion tube by a resilient member, and including a position sensor, which generates a signal indicative of a position of the distal tip relative to the distal end of the insertion tube, which changes in response to deformation of the resilient member;

advancing the probe within the body cavity so that the distal tip engages and applies a pressure against the tissue, thereby causing the resilient member to deform; and processing the signal while the distal tip engages the tissue so as to provide an indication of the pressure.

In a disclosed embodiment, advancing the probe includes bringing an electrode on the distal tip into electrical contact with the tissue, and the method includes applying electrical energy to the electrode so as to ablate a region of the tissue that is engaged by the distal tip. Applying the electrical energy may include controlling application of the energy responsively to the indication of the pressure, so that the electrical energy is applied to the electrode when the pressure is within a desired range.

There is further provided, in accordance with an embodiment of the present invention, apparatus for performing a medical procedure inside a body of a patient, the apparatus including:

a probe, which includes:
an insertion tube having a distal end for insertion into a body cavity of a patient;
a distal tip, which is flexibly coupled to the distal end of the insertion tube;
a magnetic field generator, which is disposed within the distal tip and is configured to generate a magnetic field; and
a first sensor within the distal end of the insertion tube for generating a first signal in response to the magnetic field; and
a second sensor, for disposition outside the body of the patient, for generating a second signal in response to the magnetic field;
a processor, which is coupled to receive and process the second signal so as to determine coordinates of the distal tip within the body and to receive and process the first signal so as to detect changes in a position of the distal tip relative to the distal end of the insertion tube.

The present invention will be more fully understood from the following detailed description of the embodiments thereof, taken together with the drawings in which:

DETAILED DESCRIPTION OF EMBODIMENTS

Figure 1:
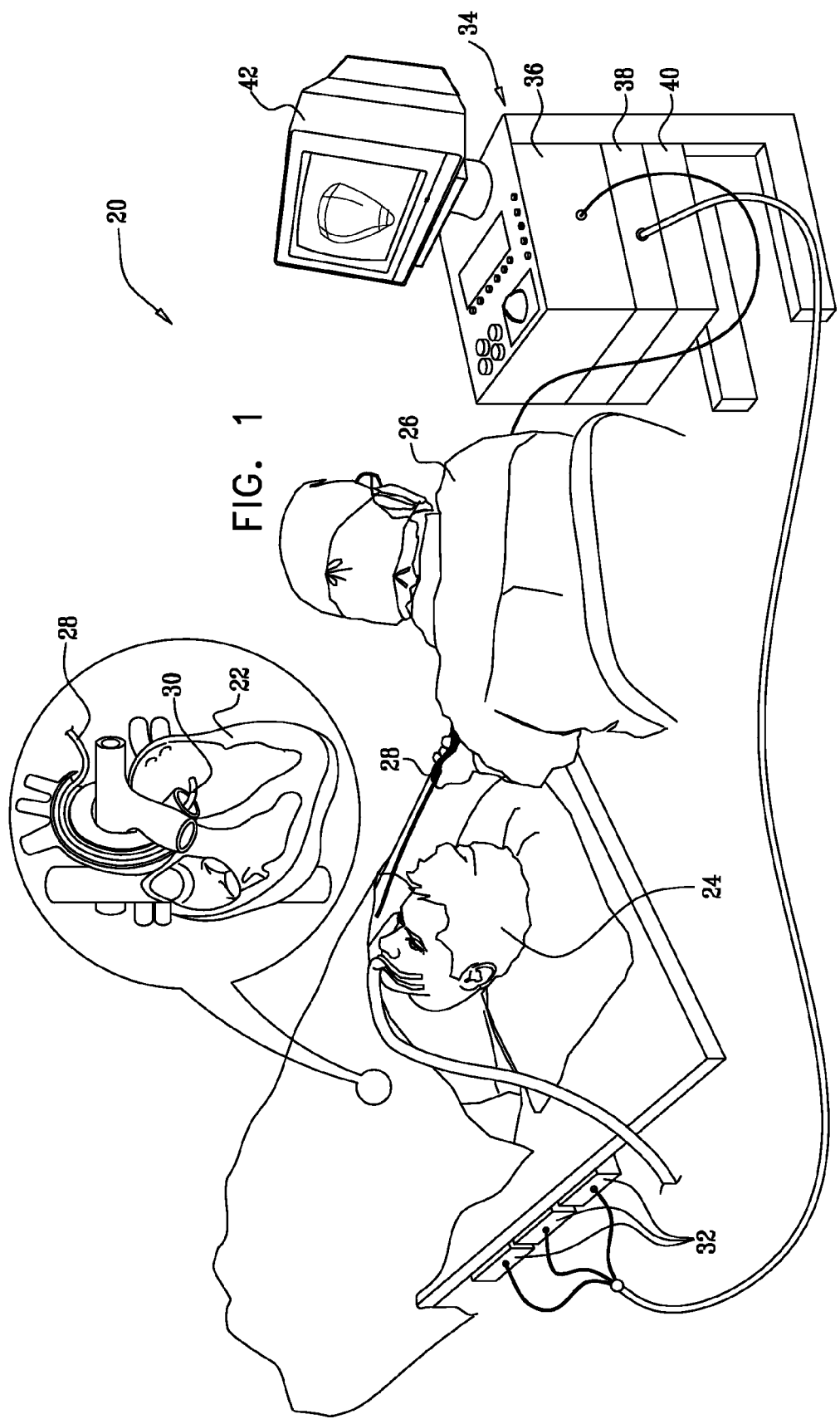
FIG. 1 is a schematic, pictorial illustration of a catheter-based medical system, in accordance with an embodiment of the present invention.

FIG. 1 is a schematic, pictorial illustration of a system 20 for cardiac catheterization, in accordance with an embodiment of the present invention. System 20 may be based, for example, on the CARTO™ system, produced by Biosense Webster Inc. (Diamond Bar, Calif.). This system comprises an invasive probe in the form of a catheter 28 and a control console 34. In the embodiment described hereinbelow, it is assumed that catheter 28 is used in ablating endocardial tissue, as is known in the art. Alternatively, the catheter may be used *mutatis mutandis*, for other therapeutic and/or diagnostic purposes in the heart or in other body organs.

An operator 26, such as a cardiologist, inserts catheter 28 through the vascular system of a patient 24 so that a distal end 30 of the catheter enters a chamber of the patient's heart 22. The operator advances the catheter so that the distal tip of the catheter engages endocardial tissue at a desired location or locations. Catheter 28 is typically connected by a suitable connector at its proximal end to console 34. The console comprises a radio frequency (RF) generator 40, which supplies high-frequency electrical energy via the catheter for ablating tissue in the heart at the locations engaged by the distal tip, as described further hereinbelow. Alternatively, the catheter and system may be configured to perform ablation by other techniques that are known in the art, such as cryoablation.

Console 34 uses magnetic position sensing to determine position coordinates of distal end 30 inside heart 22. For this purpose, a driver circuit 38 in console 34 drives field generators 32 to generate magnetic fields within the body of patient 24. Typically, the field generators comprise coils, which are placed below the patient's torso at known positions external to the patient. These coils generate magnetic fields in a predefined working volume that contains heart 22. A magnetic field sensor within distal end 30 of catheter 28 (shown in FIG. 2) generates electrical signals in response to these magnetic fields. A signal processor 36 processes these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 36 typically comprises a general-purpose computer, with suitable front end and interface circuits for receiving signals from catheter 28 and controlling the other components of console 34. The processor may be programmed in software to carry out the functions that are described herein. The software may be downloaded to console 34 in electronic form, over a network, for example, or it may be provided on tangible media, such as optical, magnetic or electronic memory media. Alternatively, some or all of the functions of processor 36 may be carried out by dedicated or programmable digital hardware components. Based on the signals received from the catheter and other components of system 20, processor 36 drives a display 42 to give operator 26 visual feedback regarding the position of distal end 30 in the patient's body, as well as status information and guidance regarding the procedure that is in progress.

Alternatively or additionally, system 20 may comprise an automated mechanism for maneuvering and operating catheter 28 within the body of patient 24. Such mechanisms are typically capable of controlling both the longitudinal motion (advance/retract) of the catheter and transverse motion (deflection/steering) of the distal end of the catheter. Some mechanisms of this sort use DC magnetic fields for this purpose, for example. In such embodiments, processor 36 generates a control input for controlling the motion of the catheter based on the signals provided by the magnetic field sensor in the catheter. These signals are indicative of both the position of the distal end of the catheter and of force exerted on the distal end, as explained further hereinbelow.

Figure 2:
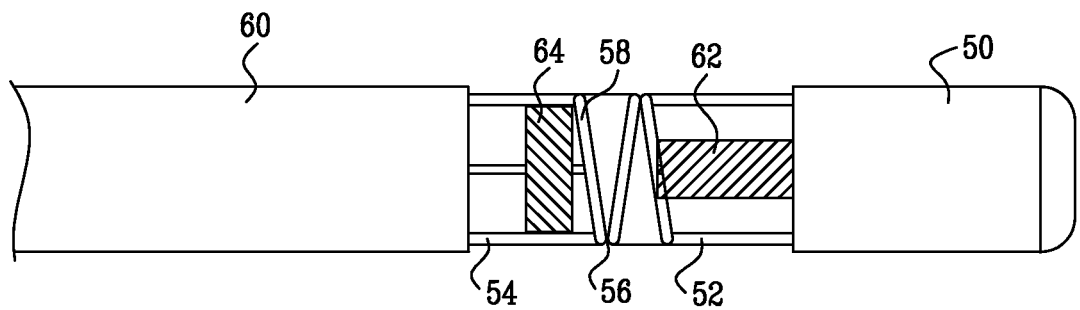
FIG. 2 is a schematic, cutaway view showing details of the distal end of a catheter, in accordance with an embodiment of the present invention.

FIG. 2 is a schematic, cutaway view of distal end 30 of catheter 28, showing details of the structure of the catheter in accordance with an embodiment of the present invention. Catheter 28 comprises a flexible insertion tube 54, with a distal tip 52 connected to the distal end of tube 54 at a joint 56. The insertion tube is covered by a flexible, insulating material 60, such as Celcon® or Teflon®. The area of joint 56 is covered, as well, by a flexible, insulating material, which may be the same as material 60 or may be specially adapted to permit unimpeded bending and compression of the joint, (This material is cut away in FIG. 2 in order to expose the internal structure of the catheter.) Distal tip 52 may be covered, at least in part, by an electrode 50, which is typically made of a metallic material, such as a platinum/iridium alloy. Alternatively, other suitable materials may be used, as will be apparent to those skilled in the art. Further alternatively, the distal tip may be made without a covering electrode. The distal tip is typically relatively rigid, by comparison with the flexible insertion tube.

Distal tip 52 is connected to the distal end of insertion tube 54 by a resilient member 58. In FIG. 2, the resilient member has the form of a coil spring, but other types of resilient components may alternatively be used for this purpose. For example, resilient member 58 may comprise a polymer, such as silicone, polyurethane, or other plastics, with the desired flexibility and strength characteristics. Resilient member 58 permits a limited range of relative movement between tip 52 and insertion tube 54 in response to forces exerted on the distal tip. Such forces are encountered when the distal tip is pressed against the endocardium during an ablation procedure. The desired pressure for good electrical contact between the distal tip and the endocardium during ablation is on the order of 20-30 grams. The spring serving as the resilient member in this embodiment may be configured, for example, to permit axial displacement (i.e., lateral movement along the axis of catheter 28) of the distal tip by about 1-2 mm and angular deflection of the distal tip by up to about 30° relative to the distal end of the insertion tube, in response to the desired pressure.

As noted above, distal tip 52 contains a magnetic position sensor 62. Sensor 62 may comprise one or more miniature coils, and typically comprises multiple coils oriented along different axes. Alternatively, sensor 62 may comprise another type of magnetic sensor, such as a Hall effect or magnetoresistive sensor, for example. The magnetic fields created by field generators 32 cause these coils to generate electrical signals, with amplitudes that are indicative of the position and orientation of sensor 62 relative to the fixed frame of reference of field generators 32. Processor 36 receives these signals via wires (not shown in the figures) running through catheter 28, and processes the signals in order to derive the location and orientation coordinates of distal tip 52 in this fixed frame of reference, as described in the patents and patent applications cited above.

In addition, insertion tube 54 contains a miniature magnetic field generator 64 near the distal end of the insertion tube. Typically, field generator 64 comprises a coil, which is driven by a current conveyed through catheter 28 from console 34. The current is generated so as to create a magnetic field that is distinguishable in time and/or frequency from the fields of field generators 32. For example, the current to field generator 64 may be generated at a selected frequency in the range between about 16 kHz and 25 kHz, while field generators 32 are driven at different frequencies. Additionally or alternatively, the operation of generators 32 and 64 may be time-multiplexed.

The magnetic field created by field generator 64 causes the coils in sensor 62 to generate electrical signals at the drive frequency of field generator 64. The amplitudes of these signals will vary depending upon the location and orientation of distal tip 52 relative to insertion tube 54. Processor 36 processes these signals in order to determine the axial displacement and the magnitude of the angular deflection of the distal tip relative to the insertion tube. (Because of the axial symmetry of the field generated by a coil, only the magnitude of the deflection can be detected using a single coil in field generator 64, and not the direction of the deflection. Optionally, field generator 64 may comprise two or more coils, in which case the direction of deflection may be determined, as well.) The readings of displacement and deflection are typically accurate to within a few tenths of a millimeter and about one degree, respectively. The magnitudes of the displacement and deflection may be combined by vector addition to give a total magnitude of the movement of distal tip 52 relative to the distal end of insertion tube 54.

The relative movement of the distal tip relative to the distal end of the insertion tube gives a measure of the deformation of resilient member 58. Generally speaking, this deformation is proportional to the force that is exerted on the resilient member, which is roughly equal to the force that is exerted on the distal tip by the heart tissue with which the distal tip is in contact. Thus, the combination of field generator 64 with sensor 62 serves as a pressure sensing system, for determining the approximate pressure exerted by the endocardial tissue on the distal tip of the catheter (or equivalently, the pressure exerted by electrode 50 against the endocardial tissue). By virtue of the combined sensing of displacement and deflection, this pressure sensing system reads the pressure correctly regardless of whether the electrode engages the endocardium head-on or at an angle. The pressure reading is insensitive to temperature variations and free of drift, unlike piezoelectric sensors, for example.

Figure 3:
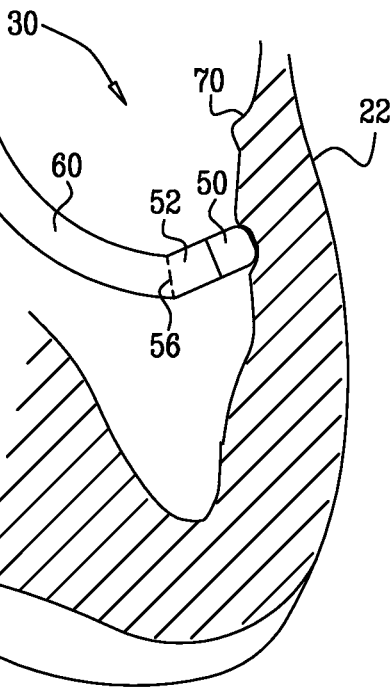
FIG. 3 is a schematic detail view showing the distal tip of a catheter in contact with endocardial tissue, in accordance with an embodiment of the present invention.

FIG. 3 is a schematic detail view showing distal end 30 of catheter 28 in contact with endocardium 70 of heart 22, in accordance with an embodiment of the present invention. Pressure exerted by the distal tip against the endocardium deforms the endocardial tissue slightly, so that electrode 50 contacts the tissue over a relatively large area. Since the electrode engages the endocardium at an angle, rather than head-on, distal tip 52 bends at joint 56 relative to the insertion tube of the catheter. The bend facilitates optimal contact between the electrode and the endocardial tissue.

Processor 36 receives and processes the signals generated by sensor 62 in response to the magnetic field of generator 64, in order to derive an indication of the pressure exerted by distal tip 52 on endocardium 70. As noted earlier, for good ablation, pressure of about 20-30 grams is desirable. Lower pressure means that there may be inadequate contact between electrode 50 and the endocardial tissue. As a result, much or all of the RF energy may be carried away by the blood inside the heart, and the tissue will be ablated inadequately or not at all. Higher pressure means that the electrode is pressing too hard against the endocardial tissue. Excessive pressure of this sort may cause severe cavitation in the tissue, leading to extensive tissue damage and possibly even perforation of the heart wall.

To avoid these eventualities, console 34 outputs an indication of the pressure measured using sensor 62 to operator 26, and may issue an alarm if the pressure is too low or too high. Optionally, RF generator 40 may be interlocked, so as to supply RF power to electrode 50 only when the pressure against the tissue is in the desired range. Alternatively or additionally, the pressure indication may be used in closed-loop control of an automated mechanism for maneuvering and operating catheter 28, as described hereinabove, to ensure that the mechanism causes the distal end of the catheter to engage the endocardium in the proper location and with the appropriate pressure against the tissue.

In an alternative embodiment, the roles of sensor 62 and magnetic field generators 32 and 64 may be reversed. In other words, driver circuit 38 may drive a magnetic field generator in distal tip 52 to generate one or more magnetic fields. The coils in generators 32 and 64 may be configured to sense and generate signals indicative of the amplitudes of the components of these magnetic fields. Processor 36 receives and processes these signals in order to determine the pressure of the distal tip against the tissue and the position coordinates of the distal tip within the heart.

Although the operation of sensor 62 and field generator 64 in sensing pressure is described above in the context of catheter-based ablation, the principles of the present invention may similarly be applied in other therapeutic and diagnostic applications that use invasive probes, both in the heart and in other organs of the body. As one example, the devices and techniques for position and pressure sensing that are implemented in system 20 may be applied, mutatis mutandis, in guiding and controlling the use of a catheter insertion sheath. If the position of the sheath is not properly controlled and excessive force is used in its insertion, the sheath may perforate the heart wall or vascular tissue. This eventuality can be avoided by sensing the position of and pressure on the distal tip of the sheath. In this regard, the term "distal tip" as used herein should be understood to include any sort of structure at the distal end of a probe that may be bent and/or displaced relative to the main body of the probe.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An ablation catheter for use in a tissue ablation procedure comprising:
    an insertion tube, the insertion tube being a flexible insertion tube, the insertion tube having a distal end for insertion into a body cavity of a patient;
    a distal tip electrode disposed at the distal end of the insertion tube and configured to be brought into contact to ablate tissue in the body cavity;
    a resilient member comprising a spring which couples the distal tip electrode to the distal end of the insertion tube and is configured to deform in response to pressure exerted on the distal tip electrode when the distal tip electrode engages the tissue during the tissue ablation procedure; and
    a magnetic position sensor disposed at the distal end of the insertion tube near the distal tip electrode for sensing a position of the distal tip electrode relative to the distal end of the insertion tube, which changes in response to deformation of the resilient member, to give a total magnitude of the movement of distal tip electrode relative to the distal end of insertion tube, so as to give a measure of the deformation of resilient member, and the magnetic position sensor is configured to generate a signal, responsively to the deformation, which is indicative of the pressure exerted on the distal tip electrode during the tissue ablation procedure;
    wherein the magnetic position sensor is configured to generate a signal indicative of the position of the distal tip electrode responsively to a magnetic field that is generated in a vicinity of the distal tip electrode;
    wherein the ablation catheter comprises a magnetic field generator within the distal end of the insertion tube for generating the magnetic field.

2. The ablation catheter according to claim 1, wherein the magnetic position sensor is configured to generate a signal indicative of an axial displacement and an orientation of the distal tip electrode relative to the distal end of the insertion tube.

3. The ablation catheter according to claim 1, wherein the magnetic position sensor is disposed in the distal end of the insertion tube, and wherein the ablation catheter comprises a magnetic field generator near distal tip electrode for generating the magnetic field.

4. The ablation catheter according to claim 1, wherein the magnetic position sensor and the magnetic field generator comprise coils.

5. The ablation catheter according to claim 1, wherein the resilient member is covered by a flexible insulating material.

6. Apparatus for performing a tissue ablation procedure on tissue inside a body of a patient, the apparatus comprising:
- a first magnetic field generator, for disposition outside the body of the patient, for generating a first magnetic field within the body;
- a probe, which comprises:
- an insertion tube having a distal end for insertion into a body cavity of a patient;
- a second magnetic field generator within the distal end of the insertion tube for generating a second magnetic field;
- a distal tip electrode, which is flexibly coupled to the distal end of the insertion tube;
- a resilient member, which couples the distal tip electrode to the distal end of the insertion tube; and
- a sensor disposed at the distal end of the insertion tube near the distal tip electrode and is configured to generate first and second signals responsively to the first and second magnetic fields, respectively; and
- a processor, which is coupled to receive and process the first signal so as to determine coordinates of the distal tip electrode within the body and to receive and process the second signal so as to detect changes in a position of the distal tip electrode relative to the distal end of the insertion tube;
- wherein the resilient member is configured to deform in response to pressure exerted on the distal tip electrode when the distal tip electrode engages tissue inside the body during the tissue ablation procedure, and wherein the changes in the position of the distal tip electrode are indicative of deformation of the resilient member,
- wherein the processor is configured to generate, responsively to the deformation, an output that is indicative of the pressure exerted on the distal tip electrode during the tissue ablation procedure.

7. The apparatus according to claim 6, wherein the changes in the position of the distal tip electrode detected by the processor comprise axial displacement of the distal tip electrode and deflection of the distal tip electrode relative to the distal end of the insertion tube.

8. The apparatus according to claim 6, wherein the sensor and the second magnetic field generator comprise coils.

9. The apparatus according to claim 6, wherein the resilient member comprises a spring.

10. The apparatus according to claim 6, wherein the resilient member is covered with a flexible insulating material.

11. The apparatus according to claim 6, wherein the processor is configured to generate a control input for automatically controlling motion of the probe within the body cavity responsively to the first and second signals.

12. Apparatus for performing a tissue ablation procedure inside a body of a patient, the apparatus comprising:
- a probe comprising:
- an insertion tube having a distal end for insertion into a body cavity of a patient;
- a distal tip electrode, which is flexibly coupled to the distal end of the insertion tube;
- a resilient member covered with a flexible insulting material, which flexibly couples the distal tip electrode to the distal end of the insertion tube;
- a magnetic field generator disposed on one end of the resilient member and configured to generate a magnetic field; and
- a magnetic sensor disposed on another end of the resilient member for generating a signal in response to the magnetic field; and
- a processor, which is coupled to receive and process the signal so as to detect changes in a position of the distal tip electrode relative to the distal end of the insertion tube,
- wherein the resilient member is configured to deform in response to pressure exerted on the distal tip electrode when the distal tip electrode engages tissue inside the body, and wherein the changes in the position of the distal tip electrode are indicative of deformation of the resilient member,
- wherein the processor is configured to generate, responsively to the deformation, an output that is indicative of the pressure exerted on the distal tip electrode.

13. A catheter for performing a tissue ablation procedure inside a body of a patient comprising:
- an insertion tube having a distal end for insertion into a body cavity of a patient;
- a distal tip electrode which is flexibly coupled to the distal end of the insertion tube;
- a spring covered with a flexible insulting material which flexibly couples the distal tip electrode to the distal end of the insertion tube;
- a magnetic field generator disposed on one end of the resilient member and configured to generate a magnetic field; and
- a magnetic sensor disposed on another end of the resilient member for generating a signal in response to the magnetic field;
- wherein the spring is configured to deform in response to pressure exerted on the distal tip electrode when the distal tip electrode engages tissue inside the body, and wherein the changes in the position of the distal tip electrode are indicative of deformation of the spring,
- wherein the processor is configured to generate, responsively to the deformation, an output that is indicative of the pressure exerted on the distal tip electrode.

14. The catheter of claim 13 wherein the spring permits axial displacement of the distal tip electrode of between approximately 1 millimeters and 2 millimeters.

15. The catheter of claim 13 wherein the spring permits angular deflection of the distal tip electrode up to approximately 30 degrees.

16. The catheter of claim 13 wherein the distal tip electrode is an RF electrode operated at a frequency range between approximately 16 kHz and 25 kHz.

* * * * *